United States Patent [19]
Subramaniam et al.

[11] Patent Number: 5,874,029
[45] Date of Patent: Feb. 23, 1999

[54] METHODS FOR PARTICLE MICRONIZATION AND NANONIZATION BY RECRYSTALLIZATION FROM ORGANIC SOLUTIONS SPRAYED INTO A COMPRESSED ANTISOLVENT

[75] Inventors: Bala Subramaniam; Said Saim; Roger A. Rajewski; Valentino Stella, all of Lawrence, Kans.

[73] Assignee: The University of Kansas, Lawrence, Kans.

Related U.S. Application Data

[60] Provisional application No. 60/012,593 Mar. 1, 1996.

[21] Appl. No.: 723,463
[22] Filed: Oct. 9, 1996
[51] Int. Cl.[6] ............................................. B29B 9/00
[52] U.S. Cl. ........................ 264/12; 264/13; 264/14
[58] Field of Search .................................. 264/7, 12, 13, 264/14

[56] References Cited

U.S. PATENT DOCUMENTS

| | | | |
|---|---|---|---|
| 4,900,558 | 2/1990 | Barry et al. | 424/461 |
| 5,043,280 | 8/1991 | Fischer et al. | 435/235.1 |
| 5,301,664 | 4/1994 | Sievers et al. | 128/200.23 |
| 5,308,648 | 5/1994 | Prince et al. | 427/212 |
| 5,344,676 | 9/1994 | Kim et al. | 427/468 |
| 5,360,478 | 11/1994 | Kurkonis et al. | 117/68 |
| 5,389,263 | 2/1995 | Gallagher | 210/729 |

FOREIGN PATENT DOCUMENTS

| | | |
|---|---|---|
| 0542314 | 5/1993 | European Pat. Off. |
| 9201446 | 2/1992 | WIPO . |
| 9501221 | 1/1995 | WIPO . |
| 9501324 | 1/1995 | WIPO . |

OTHER PUBLICATIONS

Wilcox et al; Liquid Atomization in a High Intensity Sound Field; A.I.Ch.E. Journal; vol. 11, No. 1, pp. 69–72 (1965).

Lefebvre; Arthur H.; Atomization and Sprays; pp. 136–153 (1989).

Heat Systems Ultrasonics, Inc. brochure; Sonimist Ultrasonic Spray Nozzles.

York et al.; Particle Engineering by Supercritical Fluid Technologies for Powder Inhalation Drug Delivery Respiratory Drug Delivery V, 1996, pp. 231–239.

Yeo et al.; Supercritical Antisolvent Process for Substituted Para–linked Aromatic Polyamides: Phase Equilibrium and Morphology Study; Macromolecules 1993, 26, 6207–6210.

Yeo et al.; Formation of Microparticulate Protein Powders Using a Supercritical Fluid Antisolvent; Biotechnology and Bioengineering, vol. 41, pp. 341–346 (1993).

Dixon et al.; Polymeric Materials Formed by Precipitation with a Compressed Fluid Antisolvent; AIChE Journal, Jan. 1993, vol. 39, No. 1, pp. 127–139.

Tom et al.; Formation of Bioerodible Polymeric Microspheres and Microparticles by Rapid Expansion of Supercritical Solutions; Biotechnol. Prog. 1991, 7, 403–411.

Bodmeier et al.; Polymeric Microspheres Prepared by Spraying into Compressed Carbon Dioxide; Pharmaceutical Research, vol. 12, No. 8, 1995.

(List continued on next page.)

*Primary Examiner*—Mary Lynn Theisen
*Attorney, Agent, or Firm*—Hovey, Williams, Timmons & Collins

[57] ABSTRACT

A method and an apparatus useful for the production of microparticles and nanoparticles are disclosed in which a compressed fluid and a solution including a solvent and a solute are introduced into a nozzle to produce a mixture. The mixture is then passed out of the nozzle to produce a spray of atomized droplets. The atomized droplets are contacted with a supercritical antisolvent to cause depletion of the solvent in the droplets so that particles are produced from the solute. Preferably, these particles have an average diameter of 0.6 $\mu$m or less. The invention can be used in the pharmaceutical, food, chemical, electronics, catalyst, polymer, pesticide, explosives, and coating industries, all of which have a need for small-diameter particles.

22 Claims, 9 Drawing Sheets

OTHER PUBLICATIONS

Niwa et al.; Preparations of Biodegradable Nanospheres of Water–soluble and Insoluble Drugs with D, L–lactide/glycolide Copolymer by a Novel Spontaneous Emulsification Solvent Diffusion Method, and the Drug Release Behavior, Journal of Controlled Release, 25 (1993) 89–98.

Sanchez et al.; Development of Biodegradable Microspheres and Nanospheres for the Controlled Release of Cyclosporin A; International Journal of Pharmaceutics, 99 (1993) 263–273.

Dixon, Microcelluar Microspheres and Microballoons by Precipitation with a Vapour–liquid Compressed Fluid Antisolvent; Polymer, vol. 35, No. 18 (1994).

Dixon et al; Formation of Microporous Polymer Fibers and Oriented Fibrils by Precipitation with a Compressed Fluid Antisolvent; J. Applied Polymer Science, vol. 50, 1929–1942 (1993).

Randolph et al.; Sub–Micrometer–Sized Biodegradable Particles of Poly(L–Lactic Acid) via the Gas Antisolvent Spray Precipitation Process; Biotechnol. Prog. 1993, vol. 9, No. 4.

DeBenedetti; Supercritical Fluids as Particle Formation Media; NATO ASI Series, E: Applied Sciences, vol. 273 (1994).

Yeo et al. Secondary Structure Characterization of Microparticulate Insulin Powders; J. Pharmaceutical Sciences, vol. 83, No.12, Dec. 1994.

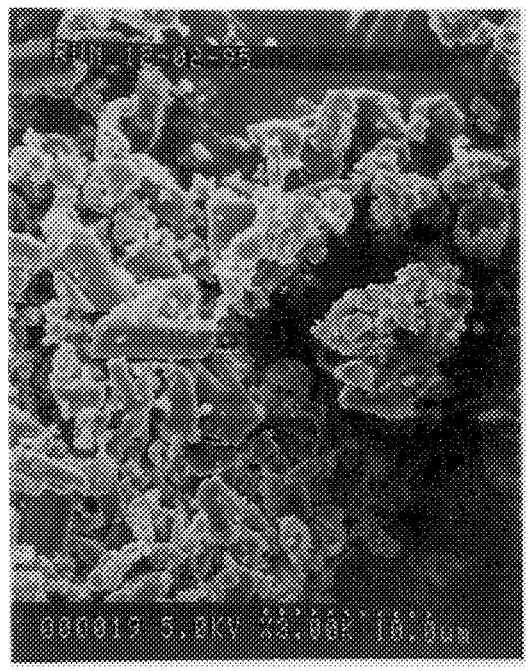
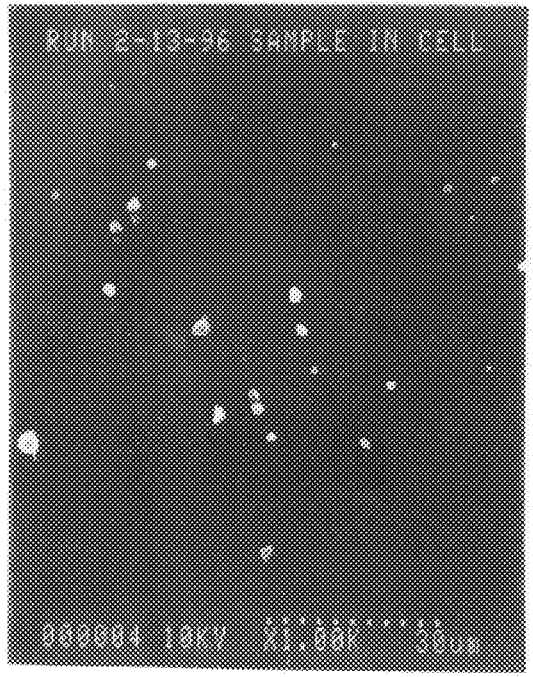
Fig. 8.
Fig. 10.

METHODS FOR PARTICLE MICRONIZATION AND NANONIZATION BY RECRYSTALLIZATION FROM ORGANIC SOLUTIONS SPRAYED INTO A COMPRESSED ANTISOLVENT

This Application claims benefit from the Provisional patent application Ser. No. 60/012,593, filed Mar. 1, 1996, and entitled RECRYSTALLIZATION OF NANOPARTICLES OF SUBSTANCES SOLUBLE IN AN ORGANIC SOLVENT; AND COATING OF MICROPARTICLES INSOLUBLE IN AN ORGANIC SOLVENT WITH A SUBSTANCE SOLUBLE IN THE SAME ORGANIC SOLVENT, the teachings of which are incorporated herein by reference.

1. Field of the Invention

The present invention relates to a method and an apparatus for particle micronization and nanonization (i.e., the creation of particles having sizes smaller than 100 μm and 1 μm, respectively) by recrystallization or precipitation from solutions using near-critical and supercritical antisolvents. More particularly, the method and apparatus of the present invention involve spraying the solution into a supercritical antisolvent using a spray nozzle. The present invention is especially suited for the production of particles having an average diameter of 0.6 μm or less.

2. Background of the Invention

A number of industries have experienced a long-felt need for particle micronization and nanonization (as those terms are used herein). The need for an apparatus or method capable of producing sub-micron and nanosized particles is particularly pronounced in the field of pharmaceutics.

Colloidal drug delivery systems have been extensively investigated for either sustained release or for targeted distribution of drugs (Allemann, E., Gurny, R., Doelker, E., Skinner, F. S., and Schutz H., 1994, Distribution, kinetics and elimination of radioactivity after intravenous and intramuscular injection of $^{14}$C-savoxepine loaded poly(D,L-lactic acid) nanospheres to rats. *J. Controlled Release*, 29:97–104). Drug delivery vehicles in the form of injectable microparticulate systems or implantable devices are a convenient way of administering drug products. Some of the advantages include reduction in injection frequency and better attenuation of peak/trough drug levels. The drugs are dispersed within a polymeric phase and released by diffusion and/or surface erosion (Heller, J., 1984, In Medical Applications of Controlled Release, pp. 69–101, Langer, R. S. and Wise, D. L., Eds., CRC Press, Boca Raton, Fla.). Pure drugs and drug-loaded microspheres smaller that 150 μm are suitable for injection (Yeo, S.-D., Lim, G.-B., Debenedetti, P. G., and Bernstein, H., 1993, Formation of microparticulate protein powders using supercritical fluid antisolvents. *Biotech. & Bioeng.* 41:341–346).

Nanoparticles are especially suitable for intravenous injection and are more desirable if drug bioavailability is particle-size dependent, as in the case of poorly water-soluble drugs with low dissolution rates. In such cases, the dissolution rates can be enhanced by increasing the mass-transfer area (i.e., by reducing particle size or by increasing particle surface area). In fact, it has been reported that nanoparticles smaller than 0.5 μm could cross Peyer's patches and the mesentery on the surface of gastrointestinal mucosa to deliver a drug to the systemic circulation (Jani, P., Halbert, G. W., Langbridge, J., and Florence, A. T., 1990, Nanoparticle uptake by the rat gastrointestinal mucosa: quantitation and particle-size dependency. *J. Pharm. Pharmacol.* 42:821–826; Tomlinson, E., 1983, Microsphere delivery systems for drug targeting and controlled release. *Int. J. Pharm* 4:49–57).

The development of environmentally benign methods for the production of either solvent-free nanoparticles of poorly water-soluble pure drugs or drug-loaded sub-micron particles for controlled drug release is thus highly desirable. For example, Cyclosporin A (CyA) is a highly lipophilic cyclic peptide poorly soluble in water. It is the immunosuppressant of choice for the prevention of allograft rejection of transplanted bone marrow, kidney, heart, liver, lung, pancreas, and skin, and appears to be efficacious in the treatment of autoimmune diseases such as diabetes mellitus and rheumatoid arthritis (Borel, J. F. and Gunn, H. C., 1985, Cyclosporine as a new approach to therapy of autoimmune diseases. *Ann. N.Y. Acad. Sci.* 475:307–319; Sanchez, A., Vila-Jato, J. L., and Alonso, M. J., 1993, Development of biodegradable microspheres and nanospheres from the controlled release of cyclosporin A. *Int. J. Pharm.* 99:263–273). At present, dosage forms of CyA (Sandimmun® intravenous and oral solutions) are not therapeutically effective due to slow and highly variable absorption. Therefore, an oleous solution of this drug (Cremophor® EL) is administered daily for 2–6 hours during the first week of therapy. However, Cremophor® EL has been reported to be nephrotoxic (Luke, D. R., Kasiske, B. L., Matzke, G. R., Awni, W. M., and Keane, W. F., 1987, Effects of cyclosporine on the isolated perfused rat kidney. *Transplantation* 43:795–799), and to cause anaphilactoid reactions (Cavanak, T. and Sucker, H., 1986, Formulation of dosage forms. *Prog. Allergy* 38:65–72). The low water solubility of CyA has prevented the development of alternative dosage forms. Other dosage forms such as liposomes and lipophilic carriers have limited in vitro and in vivo stability.

A variety of other poorly water-soluble drugs whose bioavailability depends on particle size exist, including camptothecin, piposulfam, steroid A, and indomethacin. Camptothecin, for instance, is an anti-cancer drug; however, its poor water solubility also limits its effectiveness and can induce toxicity. Other soluble derivatives of camptothecin are in their second phase of clinical trials; however, derivatives may not have the therapeutic effectiveness of the parent drug. For instance, the sodium salt of camptothecin is only 10% as active as camptothecin.

Conventional techniques for particle-size reduction currently practiced suffer from many disadvantages. These conventional techniques involve either mechanical comminution (crushing, grinding, and milling) or recrystallization of the solute particles from liquid solutions. The limitations of mechanical comminution for particle-size reduction are the shock sensitivity associated with the solid, thermal degradation due to heat generation during mechanical comminution, lack of brittleness of some solids (e.g., most polymers), and chemical degradation due to exposure to the atmosphere.

Conventional recrystallization of solutes from liquid solutions exploits the dependence of a compound's solubility on temperature and/or mixture composition. By changing the temperature, or adding antisolvents to selectively remove the solvent in which the solid is solubilized, the desired material may be precipitated or crystallized from solution to form particles. Crystallization by either solvent evaporation or solvent extraction of a solute usually requires the use of toxic organic antisolvents, surfactants and oils, and yields wet particles that require further drying to remove traces of adsorbed solvent residues. Freeze drying tends to produce particles with broad size distribution that require further drying. Spray drying usually requires evaporation of solvent in a hot fluidized air bed. The high temperatures can degrade sensitive drugs and polymers. Monodisperse particle-size distribution with consistent crystal structure and crystalline properties is also difficult to attain using the above-noted techniques.

Within the last decade, processes for the production of micron and sub-micron sized particles have emerged that use either a supercritical fluid (i.e., a fluid whose temperature and pressure are greater than its critical temperature ($T_c$) and critical pressure ($P_c$)), or compressed fluids in a liquid state. It is well known that at near-critical temperatures, large variations in fluid density and transport properties from gas-like to liquid-like can result from relatively moderate pressure changes around the critical pressure (0.9–1.5 $P_c$) While liquids are nearly incompressible and have low diffusivity, gases have higher diffusivity and low solvent power. Supercritical fluids can be made to possess an optimum combination of these properties. The high compressibility of supercritical fluids (implying that large changes in fluid density can be brought about by relatively small changes in pressure, making solvent power highly controllable) coupled with their liquid-like solvent power and better-than-liquid transport properties (higher diffusivity, lower viscosity and lower surface tension compared with liquids), provide a means for controlling mass transfer (mixing) between the solvent containing the solutes (such as a drug or polymer, or both) and the supercritical fluid.

The two processes that use supercritical fluids for particle formation and that have received considerable attention in the recent past are: (1) Rapid Expansion of Supercritical Solutions (RESS) (Tom, J. W. Debenedetti, P. G., 1991, The formation of bioerodible polymeric microspheres and microparticles by rapid expansion of supercritical solutions. *BioTechnol. Prog.* 7:403–411), and (2) Gas Anti-Solvent (GAS) Recrystallization (Gallagher, P. M., Coffey, M. P., Krukonis, V. J., and Klasutis, N., 1989, GAS antisolvent recrystallization: new process to recrystallize compounds in soluble and supercritical fluids. *Am. Chem. Sypm. Ser.*, No. 406; Yeo et al. (1993); U.S. Pat. No. 5,360,478 to Krukonis et al.; U.S. Pat. No. 5,389,263 to Gallagher et al.).

In the RESS process, a solute (from which the particles are formed) is first solubilized in supercritical $CO_2$ to form a solution. The solution is then sprayed through a nozzle into a lower pressure gaseous medium. Expansion of the solution across this nozzle at supersonic velocities causes rapid depressurization of the solution. This rapid expansion and reduction in $CO_2$ density and solvent power leads to supersaturation of the solution and subsequent recrystallization of virtually contaminant-free particles. The RESS process, however, is not suited for particle formation from polar compounds because such compounds, which include drugs, exhibit little solubility in supercritical $CO_2$. Cosolvents (e.g., methanol) may be added to $CO_2$ to enhance solubility of polar compounds; this, however, affects product purity and the otherwise environmentally benign nature of the RESS process. The RESS process also suffers from operational and scale-up problems associated with nozzle plugging due to particle accumulation in the nozzle and to freezing of $CO_2$ caused by the Joule-Thompson effect accompanying the large pressure drop.

In the GAS process, a solute of interest (typically a drug, polymer or both) that is in solution or is dissolved in a conventional solvent to form a solution is sprayed, typically through conventional spray nozzles, such as an orifice or capillary tube, into supercritical $CO_2$ which diffuses into the spray droplets causing expansion of the solvent. Because the $CO_2$-expanded solvent has a lower solubilizing capacity than pure solvent, the mixture can become highly supersaturated and the solute is forced to precipitate or crystallize.

The GAS process enjoys many advantages over the RESS process. The advantages include higher solute loading (throughput), flexibility of solvent choice, and fewer operational problems in comparison to the RESS process. In comparison to other conventional techniques, the GAS technique is more flexible in the setting of its process parameters, and has the potential to recycle many components, and is therefore more environmentally acceptable. Moreover, the high pressure used in this process (up to 2,500 psig) can also potentially provide a sterilizing medium for processed drug particles; however, for this process to be viable, the selected supercritical fluid should be at least partially miscible with the organic solvent, and the solute should be preferably insoluble in the supercritical fluid.

Gallagher et al. (1989) teach the use of supercritical $CO_2$ to expand a batch volume of a solution of nitroguanadine and recrystallize particles of the dissolved solute. Subsequent studies disclosed by Yeo et al. (1993) used laser-drilled, 25–30 $\mu$m capillary nozzles for spraying an organic solution into $CO_2$. Use of 100 $\mu$m and 151 $\mu$m capillary nozzles also has been reported (Dixon, D. J. and Johnston, K. P., 1993, Formation of microporous polymer fibers and oriented fibrils by precipitation with a compressed fluid antisolvent. *J. App. Polymer Sci.* 50:1929–1942; Dixon, D. G., Luna-Barcenas, G., and Johnson K. P., 1994, Microcellular microspheres and microballoons by precipitation with a vapour-liquid compressed fluid antisolvent. *Polymer* 35:3998–4005).

One of the drawbacks of such capillary nozzles is that they are not adequate for forming extremely small droplets necessary to produce sub-micron particles having an average diameter less than 0.6 $\mu$m. Moreover, when attempting to atomize a solution that contains a solute in either high concentration or in the form of a polymer, rapid depletion of the solvent from the spray solution upon contact with $CO_2$ causes its viscosity to increase (as used herein, the term "spray solution" denotes a spray that has exited a nozzle or orifice which may or may not have undergone some degree of atomization). This effect hinders the atomization process in one or both of two ways: (1) nucleation takes place prior to secondary atomization and/or, (2) relatively large spray droplets are formed resulting in the formation of relatively large particles (i.e., particles having an average size greater than one $\mu$m).

Lower viscosity and/or lower surface tension solutions (either as a result of lower concentration of solute, or the nature of the solvent, or of both) can be easily atomized with a capillary nozzle; however, it appears that interphase mass transfer rates between the $CO_2$-rich phase and the solution droplets are low enough that significant droplet agglomeration occurs prior to crystallization, thereby resulting in the formation of large particles.

Randolph, T. W., Randolph, A. D., Mebes, M., and Yeung, S., 1993, Sub-micrometer-sized biodegradable particles of poly (L-Lactic Acid) via the "Gas Antisolvent Spray Precipitation Process", *Am. Chem. Soc. and Am. Inst. Chem. Eng.* 9:429–435, report the results of attempts made to overcome the disadvantages noted above by using an electrically-activated, ultrasonic (Sono-tek) atomizer, operated at 120 kHz (see FIG. 1 of Randolph et al. (1993)). Apparently, the electrical atomizer was viewed as a means to impart more energy into the solution for the purpose of improving atomization, and therefore for reducing particle size. Randolph et al. (1993), however, report no significant reduction in particle size obtained using the electrically-activated, Sono-tek atomizer compared to the process using a 75-$\mu$m capillary nozzle. Randolph et al. (1993) concluded that mass transfer between the spray droplets and the anti-solvent phase, rather than initial droplet size, controls particle size.

Based on the referenced investigations, it will be appreciated that the main impediments for the production of sub-micron particles using the conventional GAS process are premature expansion of the liquid solution spray droplets which result in premature solute crystallization, and low mass transfer rates. Premature crystallization (or precipitation) can be especially hindering to the atomization process when spraying solutions with high polymer and/or drug concentrations. Low interphase mass transfer rates can result in drop coalescence or agglomeration before nucleation and crystallization can occur. Conventional GAS recrystallization processes also do not provide means for controlling or substantially increasing mass transfer rates, and therefore for controlling particle size.

SUMMARY OF THE INVENTION

The present invention substantially overcomes the impediments noted above, and provides a method and an apparatus useful for the production of microparticles and nanoparticles. The invention can be used in the pharmaceutical, food, chemical, electronics, catalyst, polymer, pesticide, explosive, and coating industries, all of which can benefit from a decrease in particle size and concomitant increase in particle surface area.

The present invention provides a method and apparatus that may be employed to produce rapidly an extremely fine spray of droplets at a rate of atomization that exceeds the rate of solvent mass transfer (i.e., the transfer of antisolvent into the droplet phase and the contemporaneous solvent depletion from the spray droplet into the antisolvent). The present invention further provides a method and an apparatus that may be employed to cause the mass transfer rate at which solvent depletion occurs (1) to be fast enough to cause nucleation and crystallization, and (2) to exceed the rate at which substantial coalescence of finer droplets into larger droplets can occur.

The ultimate size of particles depends on two important factors: atomization rates and mass transfer rates. For secondary atomization to take place, mass transfer rates should be slower than atomization rates in order to prevent crystallization from taking place prior to secondary atomization. However, mass transfer rates should not be so slow as to allow droplet coalescence to occur prior to solute crystallization. Thus, an optimum mass transfer rate exists for producing sub-micron particles.

The invention provides means for both increasing atomization rates as well as for controlling and/or maximizing mass transfer rates between the antisolvent and the solvent. Atomization rates are increased through the use of a spray nozzle. Mass transfer rates are increased both by (1) reducing the atomized spray droplet size (resulting in an increase in specific surface area), and (2) increasing the concentration gradients between the droplet phase and the antisolvent phase by passing a turbulent flow of solvent-free $CO_2$ over the spray droplets. The driving force for mass transfer is maintained at a maximum level since the phase surrounding the droplet is continuously replenished with virtually solvent-free carbon dioxide.

In more detail, a method and apparatus for forming particles are disclosed that include the steps of: (1) introducing a solution (including solute(s) dissolved in a solvent) and a compressed gas (i.e., an energizing gas) into a nozzle; and (2) causing the compressed gas to flow through the nozzle under conditions such that the solution forms a spray of atomized droplets at the nozzle exit. In one embodiment, the solution and compressed gas flow through separate channels of the nozzle. The compressed gas exits the nozzle at a velocity such that the spray is shattered into extremely small droplets at the nozzle exit. The wave-front established at the nozzle exit as a result of the high velocity can be near-sonic or ultrasonic. The atomized spray of droplets is brought into contact with the supercritical antisolvent to cause depletion of the solvent in the atomized spray droplets so that particles are formed from the solute. Contact between the extremely small spray droplets and a turbulent stream of virtually pure antisolvent results in high solvent depletion rates, i.e. high mass transfer rates, and low probability for droplet coalescence.

The method and apparatus of the present invention are suitable for the production of particles having an average particle diameter of up to 10 $\mu$m, and preferably may be used in the production of particles having an average diameter of up to 0.6 $\mu$m. In one embodiment, the antisolvent (such as $CO_2$) may be employed as both the antisolvent and the compressed gas which flows through the nozzle.

In another embodiment, a "buffer" gas consisting of helium, air, nitrogen, oxygen, or a mixture of these gases with carbon dioxide or some other supercritical fluid, may be used as an energizing gas. This energizing gas, which may have a lower antisolvent power than pure antisolvent, thus forms a buffer zone (i.e., a boundary layer) between the atomized spray exiting the nozzle and the antisolvent into which the atomized spray is directed. An important purpose of this buffer zone is to control the mass-transfer rate between the dispersed droplet phase and the antisolvent phase. The ability to control the mass-transfer rate translates into an ability to control particle size. The buffer zone extends from the tip of the nozzle to the boundary between the energizing gas and the antisolvent phase, and may be defined as the region around the nozzle where local concentrations of energizing gas, solvent, and solute are substantially different (more than a 10% difference) from those of the background antisolvent phase.

If the energizing gas is pure antisolvent, then the fluid phase in the vicinity of the nozzle tip will be nearly pure antisolvent and mass transfer rates between the spray droplets and the antisolvent phase will be high. If the energizing gas is either a light gas or a supercritical fluid with substantially lower antisolvent power than the bulk phase, little solvent expansion, and therefore little crystallization, occurs within the buffer zone. Crystallization is thus delayed until the droplets reach the antisolvent phase, preferably when secondary atomization has taken place. This flexibility in the nature and antisolvent power of the energizing gas also provides a means to control the rate of interphase mass transfer in the buffer zone, close to the tip of the nozzle where atomization takes place. Mass transfer rates in the buffer zone, where the atomization process takes place, can thus be optimized. Mass transfer rates are highest if the compressed gas consists of pure antisolvent, lowest if the compressed gas is light gas, and intermediate if the compressed gas consists of a mixture of antisolvent/light gases. This flexibility is especially attractive when recrystallizing particles from highly viscous or nearly saturated solutions.

BRIEF DESCRIPTION OF THE DRAWINGS

FIG. 1 is a schematic of the apparatus for the conventional GAS recrystallization from organic solutions.

Figure 7A:
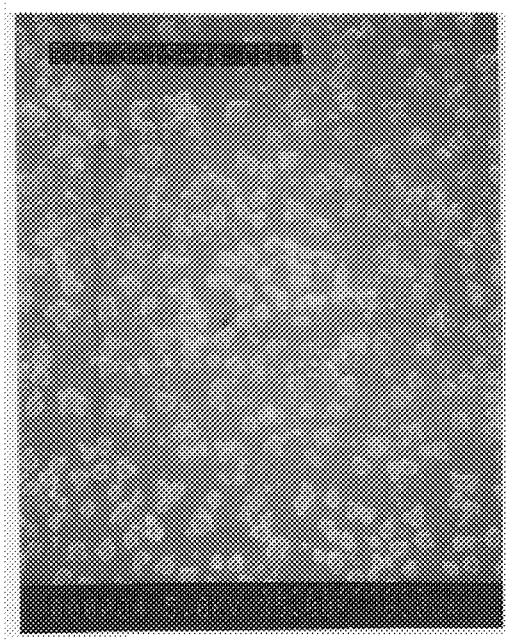

FIGS. 7a and b are a pair of SEM micrographs (5,000× and 9,900× magnification, respectively) of hydrocortisone nanonized by recrystallization from a 30 mg/ml DMSO solution using the nozzle of the present invention (compressed $CO_2$ is used as energizing gas and as antisolvent).

FIG. 8 is an SEM micrograph (3,000× magnification) of hydrocortisone micronized by recrystallization from a 30 mg/ml DMSO solution using the nozzle of the present invention (He is used as energizing gas and compressed $CO_2$ is used as antisolvent).

Figure 9A:
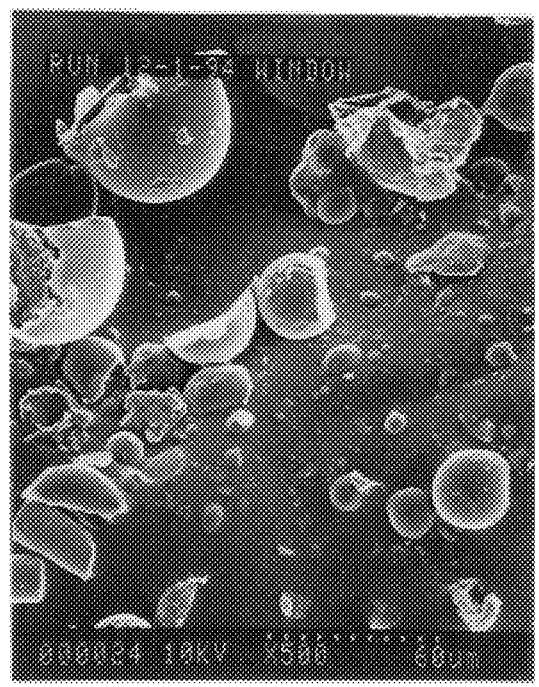
Figure 9B:
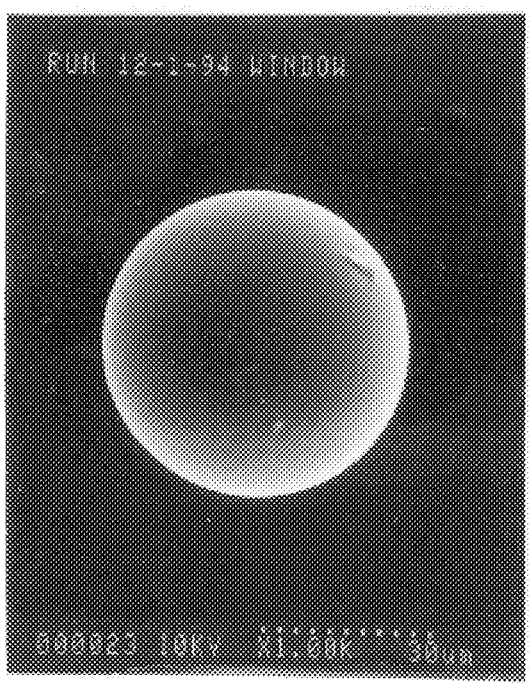

FIGS. 9a and b are a pair of SEM micrographs (500× and 1,000× magnification, respectively) of polylactic-glycolic acid polymer (RG503H) micronized by recrystallization from a 10 mg/ml ethyl acetate solution using the conventional GAS process with a 100 μm capillary nozzle.

FIG. 10 is an SEM micrograph (1,000× magnification) of RG503H micronized by recrystallization from a 10 mg/ml ethyl acetate solution using the nozzle of the present invention (compressed $CO_2$ is used as energizing gas and as antisolvent).

Figure 11A:
Figure 11B:
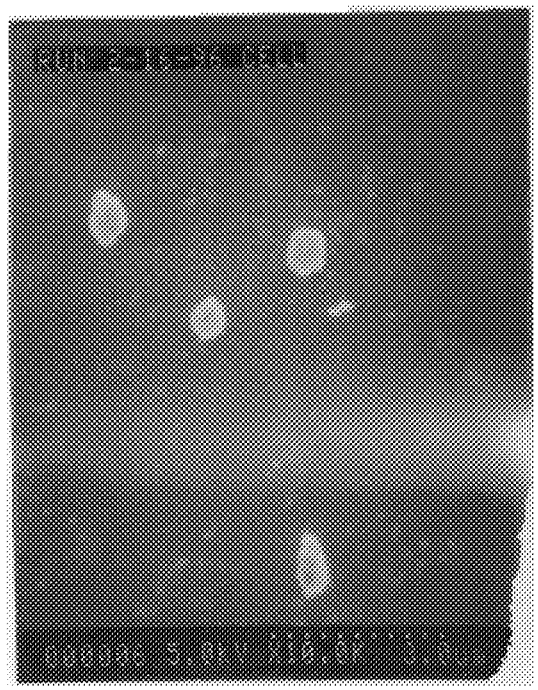

FIGS. 11a and b are a pair of SEM micrographs (1,000× and 10,000× magnification, respectively) of Ibuprofen nanonized by recrystallization from a 30 mg/ml DMSO solution using the nozzle of the present invention (compressed $CO_2$ is used as energizing gas and as antisolvent).

Figure 12:
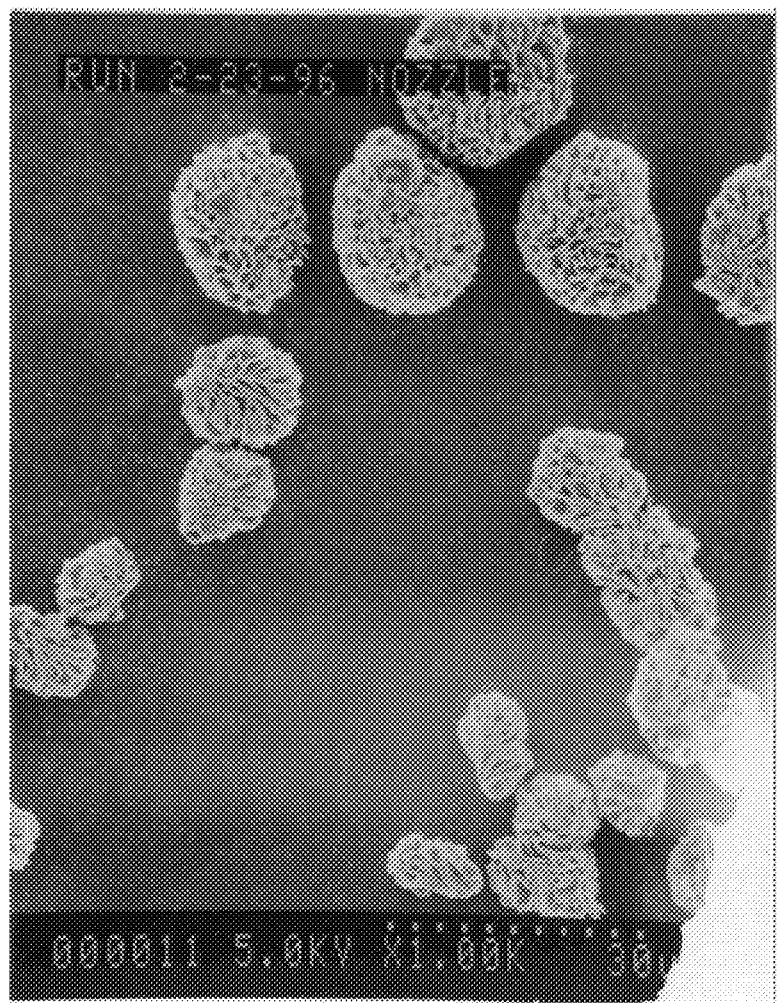

FIG. 12 is an SEM micrograph (1,000× magnification) of micronized camptothecin by recrystallization from a 5 mg/ml DMSO solution using the nozzle of the present invention (compressed $CO_2$ is used as energizing gas and as antisolvent).

Figure 13A:
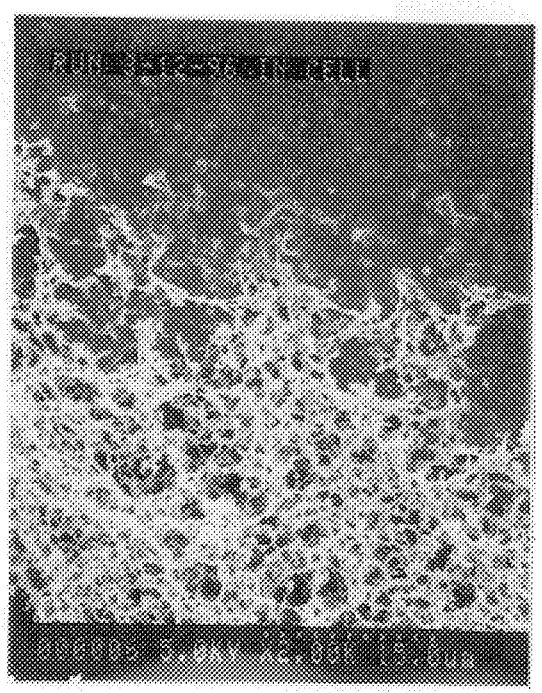

FIG. 13a and b are a pair of SEM micrographs (2,000× and 15,000× magnification, respectively) of camptothecin nanonized by recrystallization from a 5 mg/ml DMSO solution using the nozzle of the present invention (compressed $CO_2$ is used as energizing gas and as antisolvent).

DETAILED DESCRIPTION OF THE PREFERRED EMBODIMENT

The following Examples set forth are techniques, compositions, and system parameters, as well as test results demonstrating that the present invention may be employed to produce particles having an average size of less than 10 μm, and preferably less than 0.6 μm. It is to be understood, however, that these examples are presented by way of illustration only and that nothing therein should be taken as a limitation upon the overall scope of the invention.

Definitions

As used herein, the term "supercritical fluid" means either a fluid simultaneously above its critical temperature ($T_c$) and pressure ($P_c$), or a fluid suitable for use as a supercritical antisolvent. In the practice of the present invention, and as used herein, "supercritical fluid" means the temperature of the fluid is in the range of 1.01 $T_c$ to 5.0 $T_c$ and the pressure of the fluid is in the range of 1.01 $P_c$ to 8.0 $P_c$.

As used herein, the temperature and pressure of a "near-critical fluid" are in the range of 0.8 $T_c$ to 0.99 $T_c$ and 0.8 $P_c$ to 0.99 $P_c$, respectively.

As used herein, the terms "compressed gas," "energizing gas," and "compressed fluid" are interchangeable.

As used herein, the term "micronization" means the production of particles having an average diameter of 1–100 μm.

As used herein, the term "nanonization" means the production of particles having an average diameter of less than 1 μm.

As used herein, the term "diameter" refers to the average diameter of the particles as inferred from SEM micrographs.

EQUIPMENT AND EXPERIMENTAL PROCEDURES FOR EXAMPLES 1–4

Figure 1:
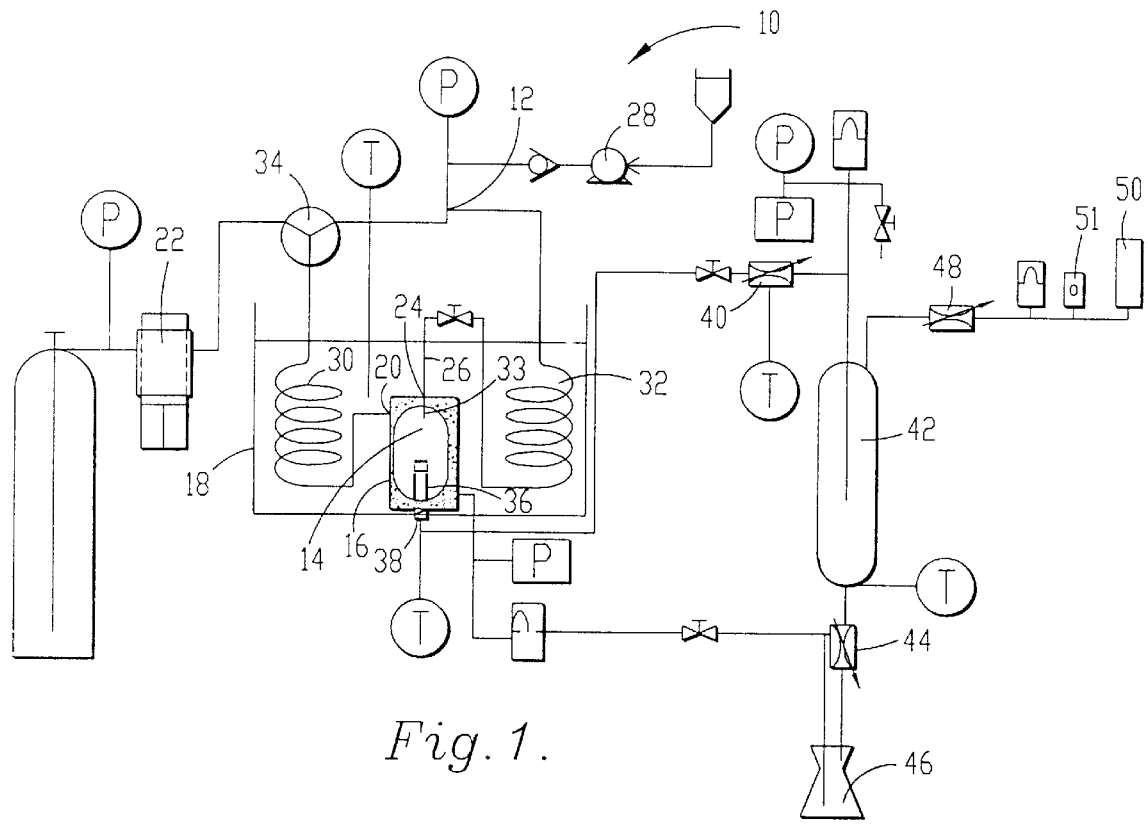

FIG. 1 shows a schematic of the apparatus 10 used for particle recrystallization from organic solvents using the conventional GAS process. The experimental unit 10 allows GAS experiments to be conducted in either batch or semi-continuous mode at pressures up to 5,000 psi and temperatures up to 70° C. The mixing of solvent and antisolvent occurs at two different locations 12, 14 within the unit. Unit 10 provides versatility in setting the operating parameters.

The unit 10 is built around a 65 ml high pressure Jerguson gauge (Burlington, Mass.) view cell 16. The cell 16 is equipped with a sapphire window that allows viewing of the expansion and crystallization process. The cell 16 is housed in a heated, isothermal, transparent acrylic water bath 18. This water bath 18 is used for maintaining the cell 16 at a desired temperature (20°–70° C.). When the bath temperature is stable at a desired value, $CO_2$ is pumped through the top side port 20 of the cell 16 with an ISCO (Lincoln, Nebr.) 260D syringe pump 22 at a constant rate (typically 5 ml/min. of liquid $CO_2$) until the pressure in the cell 16 reaches a desired level (1,500 psi). When temperature and pressure in the cell 16 are stabilized, the organic solution (DMSO or ethyl acetate solution of drug and/or polymer) is metered from the top central port 24 of the cell 16 through a stainless steel, 1/16" O.D., 100 μm I.D. capillary nozzle tubing 26 using a Milton Roy (Riviera Beach, Fla.) 396–89 minipump 28. It is found that a minimum solution flow rate of 2.5 ml/min. is needed to consistently obtain a jet spray. Both fluids are preheated to operating temperature by passing through heat exchangers 30, 32 housed together with the cell 16 in the water bath 18.

Fresh $CO_2$ and the organic solution streams thus mix at location 14, which is just downstream of the nozzle tip 33 at the top of the cell 16. A cloudy zone about 1 cm long is seen to form in this area indicating intimate mixing of the fluids and particle formation. Solvent depletion from the spray droplets causes the drug and/or polymer dissolved in the organic solvent to nucleate. The resulting particles descend down the cell. Alternatively, the streams can be premixed prior to reaching the nozzle tip 33 using the two-way valve 34.

Particles descending down the cell 16 either adhere to the cell walls or are collected on a 6" long glass rod 36. Particles larger than 0.5 μm leaving the view cell chamber are retained on a 0.5 μm stainless steel frit housed in the T-shaped fitting at the central bottom port 38. A thermocouple inserted through this fitting is used to monitor the cell temperature. The drug and/or polymer depleted mixture of $CO_2$ and organic solution then flows through a step-motor controlled, heated micrometering valve assembly 40. Upon expansion to a subcritical pressure (typically close to atmospheric pressure), the mixture separates into an organic liquid phase and a $CO_2$ gas phase. Phase separation takes place in the flash drum 42; the organic solution flows through a micrometering valve 44 and is collected in a vessel 46. The solution then may be analyzed for drug and polymer content. $CO_2$ is vented through a second micrometering valve 48, a rotameter 51, and an electronic mass flowmeter 50.

Typically, the solution is pumped for 15 minutes in order to produce a statistically representative sample of drug and/or polymer microparticles. Following this, the flow of organic solution is stopped while the $CO_2$ flow is continued for another 1.5 hours in order to flush out any organic phase left in the cell, and to dry the collected particles. It is found that flowing $CO_2$ at 1,500 psig for 1.5 hours is adequate for flushing out the organic solvent present in the cell and for drying the particles. Following the drying period, the pressure is decreased to atmospheric level at a rate of −50 psi/min. Particle samples are collected from the cell window, the porous frit, and the glass tube, and are analyzed by scanning electron microscopy (SEM) to estimate particle size and morphology.

Accurate pressure control is essential in the highly compressible near-critical region. Pressure fluctuations in this region have a strong effect on the level of expansion of the organic solution and thus on the level of supersaturation and, consequently, on crystal growth and crystal size distribution. Pressure control in the cell 16, along with monitoring of pressure, temperature, and flow rate, are accomplished using the Camile® (Midland, Mich.) 2500 Data Acquisition and Control system. A 100 steps/revolution stepping motor, operating at 200 half-steps/revolution, is used to actuate the heated micrometering valve 54. Pressure control is achieved using an HC-11 microprocessor that interprets the output from the Camile PID controller and acts as a step-motor controller. The software program allows the microprocessor to seek a window wherein the valve will operate to provide pressure control within transducer precision (±10 psi).

Figure 2:
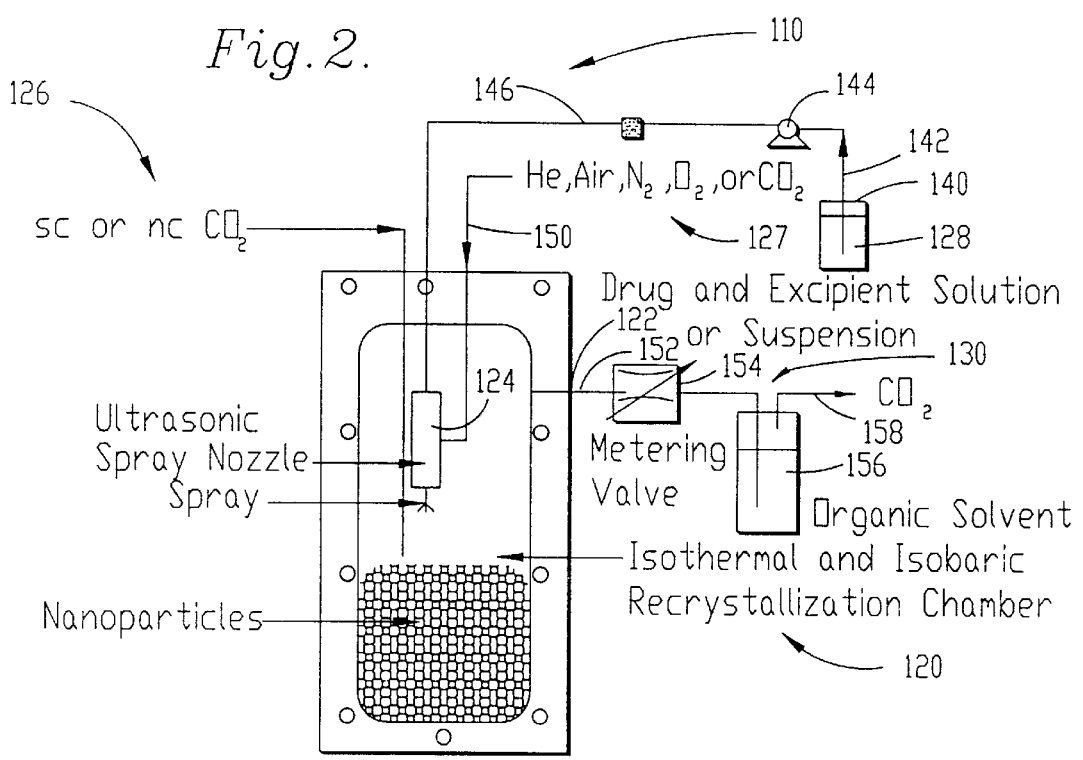
FIG. 2 is a schematic representation of an apparatus useful in the practice of the invention.

FIG. 2 shows schematically an apparatus 110 according to the present invention. Apparatus 110 is identical to apparatus 10 with the exception that the view cell serving as crystallization chamber is replaced with a larger (450 ml), stainless steel vessel that can house the nozzle. Here again, the crystallization chamber was housed in an isothermal water bath, and pressure is controlled as described previously with regard to the conventional GAS process (FIG. 1). In apparatus 110, an organic solvent such as dimethyl sulfoxide (DMSO), in which solutes such as drug, polymer, and/or excipient materials are solubilized, is also sprayed as a fine mist into a chamber containing a near-critical or supercritical antisolvent.

In more detail, apparatus 110 of the present invention includes an isothermal and isobaric recrystallization chamber 120, a spray nozzle 124, a source of supercritical (sc) or near-critical (nc) $CO_2$ 126, a source of compressed gas 127 which serves to energize the nozzle 124, a drug and excipient solution 128, an organic solvent collection vessel 156, and a $CO_2$ outlet header 130.

The drug and excipient solution is drawn from vessel 140 through line 142 by pump 144 and is discharged through line 146 into chamber 120 through line 146 as shown in FIG. 2. The nozzle 124 is attached to the end of line 146 within chamber 120. Energizing gas for the nozzle consisting of He, $N_2$, $O_2$, air, $CO_2$, other supercritical fluids, or a mixture thereof, from source 127 is admitted through line 150 into chamber 120, as shown in FIG. 2. The near-critical or supercritical fluid (antisolvent) is admitted from source 126. Alternatively, if the energizing gas is supercritical (or near-critical), source 127 also can be used for admitting the supercritical fluid into chamber 120; source 126 then may be either not employed, or used for admitting a supercritical fluid in the same composition as in source 124, or a supercritical fluid of different composition. This latter alternative can be used for either increasing or decreasing the concentration gradients between the antisolvent phase and the buffer zone. The solute-depleted organic solvent and solvent-loaded $CO_2$ are removed from chamber 120 via outlet 122 through line 152 and metering valve 154 into flash drum 156, in which $CO_2$ is allowed to separate from the liquid organic solvent. The $CO_2$ is allowed to vent from vessel 156 through vent line 158.

Figure 3:
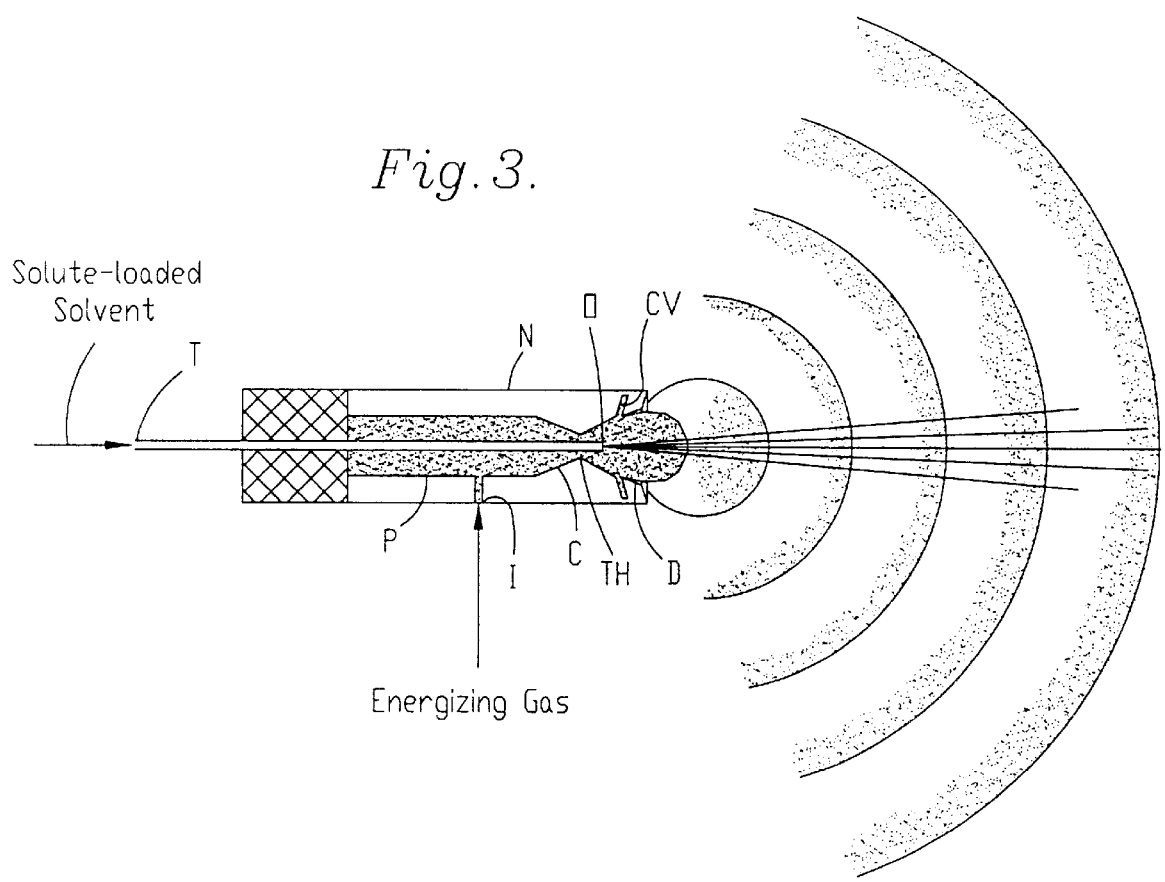
FIG. 3 is a schematic cross-sectional view of the nozzle employed in the practice of the invention.

FIG. 3 is a schematic of a nozzle (Sonimist, Farmingdale, N.Y., Model 600-1) employed in apparatus 110. This nozzle is of the convergent-divergent type. It is energized by compressed gas (conventionally a light gas such as air, He, $O_2$, or $N_2$). A sonic field is created at the throat of the nozzle as the compressed gas accelerates and reaches the velocity of sound. These sound waves impinge upon the entrance of a resonator cavity. This resonator cavity serves to produce high frequency waves which produce a chopping effect that breaks up the liquid jet comprising the solute-loaded solvent into extremely small droplets.

When spraying into ambient air, with 20–100 psig back pressure of energizing gas, the Sonimist nozzle produces a fine, evenly dispersed spray of droplets having diameters in the range of 0.1–50 $\mu$m depending on operating conditions. This size range is orders of magnitude smaller than that of conventional air atomizers. Mean droplet diameters of 1–10 $\mu$m are obtained when spraying water into ambient atmosphere. If interphase mass transfer does not significantly interfere with the atomization process, droplet sizes are expected to be even smaller when spraying into a higher pressure gaseous environment or when using organic solvents with lower surface tension and viscosity than water.

When using this nozzle, it has been found that using a chamber pressure of 1,250 psig and an energizing gas pressure of 1,850 psig provides enough energy to reduce particle size substantially. A one order of magnitude reduction in particle size (when compared to results obtained by conventional GAS recrystallization) was also observed when using only 100 psig pressure differential between the chamber held at 1,500 psig and the energizing gas ($CO_2$). Thus, the nozzle illustrated in FIG. 3 can be used in a wide range of operating conditions in order to substantially reduce particle size and to increase surface area. Furthermore, the invention may be practiced without the use of the nozzle illustrated in FIG. 3. The invention may be practiced with any nozzle that provides a means for using a gaseous (or near-critical or supercritical fluid) stream as energizing medium to atomize the sprayed solution into smaller droplets and/or to create turbulence around the spray droplets which increases the mass transfer rates between the droplet and antisolvent phases. Both converging-diverging nozzles as well as converging nozzles may be employed in the present invention.

EXAMPLES 1–4

Comparison of Particles Produced by the Conventional GAS Process and the Process of the Present Invention In these examples, the recrystallization of hydrocortisone, poly (D,L-lactide-glycolide) copolymer (RG503H), Ibuprofen, and Camptothecin was studied. The recrystallization of hydrocortisone and RG503H was performed using both the conventional GAS process as well as the present invention.

Hydrocortisone is a common anti-inflammatory agent and Ibuprofen is a common pain reliever. They were acquired from Sigma Chemical Co., St. Louis, Mo., and were used without further purification. Camptothecin is an anti-cancer drug with a very low aqueous solubility; reduction in its particle size or an increase in its particle surface area can substantially increase its dissolution rate and render it therapeutically more useful. RG503H was acquired from Henley, Montvale, N.J. It contains a 1:1 molar ratio of lactide and glycolide and has an inherent viscosity in chloroform of 0.3. RG503H is FDA approved for administration to humans, is non-toxic, non-tissue reactive, biodegrades to non-toxic products, and is particularly suited for surgical sutures. PLGA copolymers have been the subject of intense micronization and microencapsulation studies.

Certified grade DMSO and ethyl acetate (99.9% purity, Fisher Scientific, Fairlawn, N.J.), bone dry $CO_2$ (99.8% purity, Genex, Kansas City) were used without further purification. Particles were collected on a double-sided carbon tape applied to an aluminum SEM tab that was placed in the crystallization chamber prior to each experiment. Particles that were deposited on the cells walls were also collected for analysis. Particle morphology was determined by SEM (Hitachi, Model S-570). Particle size was also estimated by SEM. The SEM samples were sputter-coated with Au/Pd alloy.

Hydro-cortisone particles were redissolved in ethyl acetate, and analyzed by GC-FID for trace DMSO contamination. Effluent solutions recovered in the flash drum were also analyzed for hydrocortisone content.

The results of repeat conventional GAS recrystallization experiments are compared in Table 1. Particle size for whisker particles refers to their thickness or width. The data in Table 1 demonstrates that the average particle size for all solutes studied, including HYAFF-7 (the ethyl ester of hyaluronic acid) is reproducible, indicating that the GAS technique is a controllable and reproducible recrystallization technique.

Example 1

Figure 4:
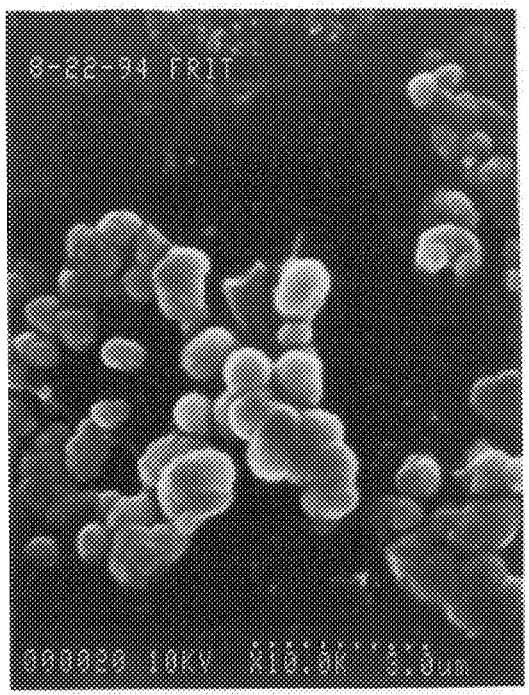
FIG. 4 is an SEM micrograph (10,000× magnification) of hydrocortisone micronized by recrystallization from a 5 mg/ml DMSO solution using the conventional GAS process with a 100 μm capillary nozzle.
Figure 5:
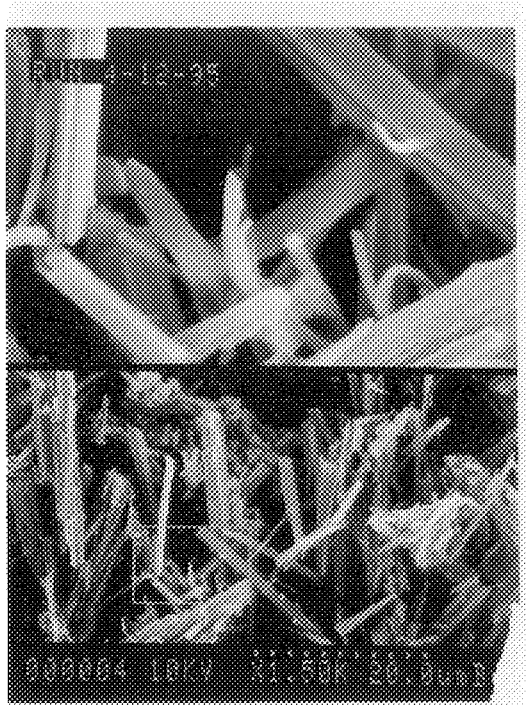
FIG. 5 is an SEM micrograph of hydrocortisone micronized by recrystallization from a 30 mg/ml DMSO solution using the conventional GAS process with a 100 μm capillary nozzle.

Comparison of Results of Recrystallization of Hydrocortisone from DMSO Solutions 1.1 Hydrocortisone Particles Produced Using the Conventional GAS Process FIG. 4 shows the SEM micrograph of hydrocortisone particles recrystallized from a 5 mg/ml DMSO solution using the 100 μm capillary nozzle (P=1,500 psi; T=35° C.; $CO_2$ flow rate=5 ml/min.; solution flow rate=2.5 ml/min.). Particles are agglomerated, nearly spherical, and range in size from 0.5–1 μm. Recrystallization of hydrocortisone from a 30 mg/ml DMSO solution yielded long (up to 1 mm),1 μm thick, whisker-shaped particles shown in FIG. 5 (P=1,500 psi; T=35° C.; $CO_2$ flow rate=5 ml/min.; solution flow rate=2.5 ml/min.; capillary I.D.=100 μm). Note that the magnification level in the upper part of micrograph (b) is five-fold greater when compared to the lower micrograph. Greater nucleation rates should result at this higher concentration, which should lead to the formation of smaller particles (Gallagher et al., 1989); however, it appears that the increase in viscosity at higher solute concentrations and the premature onset of nucleation, and crystallization prior to secondary atomization hinder the atomization process, resulting in the formation of elongated, whisker-like particles. Indeed, the increase in particle size with an increase in solute concentration was observed for all solutes recrystallized using the conventional GAS process.

Figure 6:
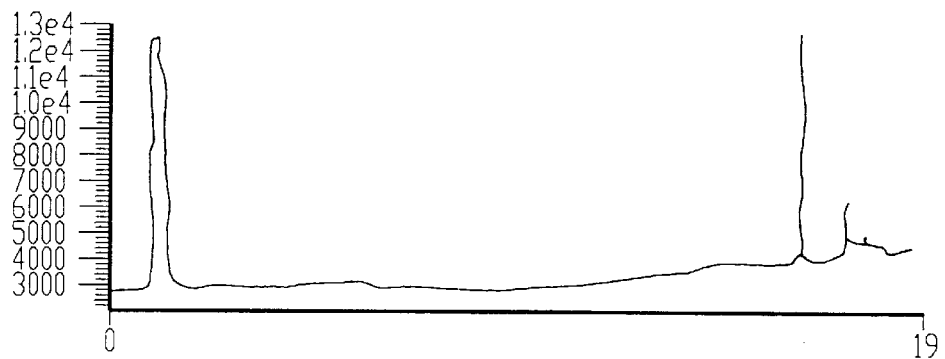
FIG. 6 is a GC-FID analysis of hydrocortisone recrystallized from a 30 mg/ml DMSO solution using the conventional GAS process with a 100 μm capillary nozzle.

Particles size is fairly reproducible. For three runs under these same conditions (30 mg/ml), particle thickness is narrowly distributed and is in the order of 1 μm. The amount of DMSO in the hydrocortisone particles was below the detection limit of the GC-FID (≈10 ppm) (FIG. 6). It thus appears that the particles are virtually solvent-free.

Analysis of effluent DMSO solutions from these three runs indicated that they contained an average concentration of hydrocortisone of 2.5±1.2 mg/ml. Hydrocortisone loss to the $CO_2$/solvent phase thus amounts to roughly 8% of all the hydrocortisone pumped into the view cell. Hydrocortisone loss could be due to (1) its partial solubility in the $CO_2$/solvent phase, or (2) a small amount of entrained, submicron particles not being retained by the 0.5 μm stainless steel filter frit.

TABLE 1

Reproducibility of Morphology and Size of Particles Formed by the Conventional GAS Recrystallization Method, as Estimated from SEM Micrographs. P = 1,500 psig; $CO_2$ Flow Rate = 5 ml/min.; Solution Flow Rate = 2.5 ml/min; Capillary Nozzle I.D. = 100 μm.

| Run | Solvent | Solute | Concentration (mg/ml) | Temp. (°C.) | Particle Morphology | Average Particle Size (μm) |
|---|---|---|---|---|---|---|
| 4-12 | DMSO | Hydrocortisone | 30 | 35 | Whisker | 1 |
| 4-14 | DMSO | Hydrocortisone | 30 | 35 | Whisker | 1 |
| 4-16 | DMSO | Hydrocortisone | 30 | 35 | Whisker | 1 |
| 12-1 | Ethyl Acetate | RG503H | 10 | 35 | Microsphere | 5–50 |
| 5-8 | Ethyl Acetate | RG503H | 10 | 35 | Microsphere | 10–20 |
| 12-16 | DMSO | RG503H | 2 | 35 | Tubes/Flakes | 25–100 |
| 12-20 | DMSO | RG503H | 2 | 35 | Tubes/Flakes | 25–100 |
| 6-6 | DMSO | HYAFF-7 | 0.5 | 40 | Resin | >100 |
| 6-8 | DMSO | HYAFF-7 | 0.5 | 40 | Resin | >100 |

1.2 Hydrocortisone Particles Produced Using the Present Invention in which Compressed $CO_2$ Was Used as Energizing Gas and as Antisolvent For a nozzle exit pressure of 1,500 psig and a temperature of 35° C., calculations indicate that an energizing pressure of roughly 6,000 psig at 55° C. is needed to obtain sonic velocities at the nozzle exit. $CO_2$ must be pumped at a rate such that a 4,500 psig back pressure is established. An experiment using 100 psig back pressure (i.e. 1,600 psig $CO_2$ supply pressure and 1,500 psig at the nozzle exit, corresponding to a $CO_2$ flow rate of 25 ml/min.) yielded hydrocortisone particles consisting of nearly spherical, 0.5–1 μm in size, and whisker-shaped particles, roughly 1 μm wide and 10 μm long. These results suggest that production of smaller particles can be achieved by using $CO_2$ at even sub-sonic velocities to energize the nozzle. Hence, while near-sonic, sonic, and supersonic compressed gas velocities are preferred for production of nanoparticles, even lower compressed gas flow rates can significantly reduce particle size when compared to the conventional GAS process where the antisolvent phase is nearly-stagnant.

FIGS. 7a and b show a pair of SEM micrographs of hydrocortisone particles recrystallized from a 30 mg/ml DMSO solution using the nozzle in FIG. 3, and $CO_2$ as energizing gas. In the recrystallization chamber, P=1,250 psig; T=35° C.; and the solution flow rate=2.5 ml/min. During the period when the solution was pumped (1 minute), the pressure of $CO_2$ at line 50 (FIG. 2) was equal to 1,850 psig, thereby providing 600 psi of back pressure. $CO_2$ temperature in source 24 (FIG. 2) was brought up to 50° C., so that upon expansion from 1,850 psig to 1,250 psig, the temperature decreased to nearly 35° C., the temperature in the crystallization chamber. This back pressure translated to a $CO_2$ flow rate of 90 ml/min. during the atomization phase. It is observed that the particles are discrete, nearly spherical, and appear to be narrowly distributed around 500 nanometers (nm). Nearly all particles are smaller than 600 nm. These results are in contrast to the 1 μm wide and nearly 1 mm long fibers observed previously (FIG. 5) when using the 100 μm capillary nozzle. Hence, a significant decrease in the average particle size is observed with the use of the present invention.

1.3 Hydrocortisone Particles Produced Using the Present Invention in which He Was Used as Energizing Gas and Compressed $CO_2$ Was Used as Antisolvent The 30 mg/ml DMSO solution of hydrocortisone was also recrystallized using He at 1,600 psig as energizing gas and $CO_2$ at 1,500 psig, 35° C. as antisolvent. FIG. 8 demonstrates that it is possible to use a light gas to energize the nozzle. Although these conditions are not optimum, the process still produces particles that are relatively small. Some particles appear to be even smaller than 1 μm. The merits of using He as opposed to $CO_2$ as energizing gas are not evident from FIG. 8; however, it is anticipated that as the solute concentration and viscosity of the solution is increased, it may be necessary to introduce a gaseous buffer such as He to avoid premature nucleation. When using a light gas to energize the nozzle, the flow rate of the supercritical fluid relative to that of the light gas should be high enough to provide sufficient antisolvent power for the supercritical fluid/light gas mixture. Use of $CO_2$ as both antisolvent and energizing gas, when possible, is advantageous over the use of a light gas as energizing gas because (a) chances for contamination are reduced, (b) the antisolvent power of $CO_2$ is not diminished, (c) required $CO_2$ flow rates are lower, and (d) solvent recovery is efficient.

Example 2

2.1 Comparison of Results of Recrystallization of RG503H Particles Produced Using the Conventional GAS Process RG503H was recrystallized from solutions of DMSO and ethyl acetate at a pressure of 1,500 psig and a temperature of 35° C. using a 100 μm capillary nozzle. Neat RG503H particles, as supplied by the vendor, are relatively large, agglomerated precipitates (>50 μm). Table 2 depicts the effect of RG503H concentration on size and morphology of RG503H recrystallized from solution. RG503H in DMSO appears to recrystallize as tubules at low concentrations, as a mixture of flakes and tubules at medium concentrations, and as precipitates of large amorphous material at higher concentrations.

Pre-mixing of $CO_2$ with the DMSO solution prior to expansion, aimed at improving mass transfer efficiency, had little effect on particle size and morphology, but caused the formation of bubbles on the surface of the flakes. These results parallel those of Dixon, D. J., Johnston, K. P. and Bodmeier, R. A., 1993, Polymeric materials formed by precipitation with a compressed antisolvent. Amer. Inst. Chem. Eng. J. 39:127–139; Randolph et al.(1993); and Bodmeier, R., H. Wang, D. J. Dixon, S. Mawson, and K. P. Johnston, 1995, Polymeric microspheres prepared by spraying into compressed carbon dioxide. Pharm. Res. 12:1211–1217. As in the previous example, these results also demonstrate the increasing difficulty of atomization and particle micronization with increasing polymer concentration due to both an increase in solution viscosity and to premature mass transfer between the solution and $CO_2$. This observation is further corroborated in FIGS. 9a and b, which show that a reduction in the viscosity and/or surface tension of the solution through a change of solvent, i.e. from DMSO (1.9 cp and 41 dyn/cm) to ethyl acetate (0.46 cp and 24 dyn/cm) led to the formation of discrete microspheres (in FIGS. 9a and b, the sprayed solution is 10 mg/ml RG503H in ethyl acetate; P=1,500 psi; T=35° C.; $CO_2$ flow rate=5 ml/min.; solution flow rate=2.5 ml/min.; capillary I.D.=100 μm). The inability to attain sub-micron particles of average size smaller than 0.6 μm using the conventional GAS process is attributed to mass transfer limitations. These are overcome in the present invention as explained earlier and as demonstrated in the following example.

TABLE 2

Micronization of RG503H by Conventional GAS Recrystallization. P = 1,500 psig; T = 35° C.; $CO_2$ flow rate = 5 ml/min.; Solution Flow Rate = 2.5 ml/min.; Capillary I.D. = 100 μm; Solvent is DMSO except for Run 6.

| Run # | Shape | Particle Size (μm) | [RG503H] (mg/ml) |
|---|---|---|---|
| 1 | whiskers | 15 | 0.5 |
| 2 | whiskers/flakes | 15/50 | 2.0 |
| 3 | whiskers/flakes | 25/>100 | 2.0 |
| 4 | flakes | 100 | 10.0 |
| 5 | amorphous | >500 | 100.0 |
| 6 | hollow microspheres | <50 | 10.0* |
| 7 | flakes with bubbles | >500 | 10.0^ |

*Solvent is ethyl acetate. ^: Premixing of solvent and $CO_2$.

2.2 RG503H Particles Produced Using the Present Invention in which Compressed $CO_2$ is used as Energizing Gas and as Antisolvent FIG. 10 shows an SEM micrograph of RG503H particles recrystallized from a 10 mg/ml ethyl acetate solution. These particles are compared with particles shown in FIGS. 19a and b, which are obtained using the conventional GAS process. Both experiments were conducted at identical conditions of pressure, temperature, and solution flow rate (1,500 psig, 35° C., and 2.5 ml/min, respectively) within the crystallization chamber, except that the particles shown in FIG. 10 were obtained using the present invention in which compressed $CO_2$ was used as energizing gas. The $CO_2$ supply pressure was 1,600 psig. Similar to the particles seen in FIGS. 9a and b, the RG503H particles in FIG. 10 are also nearly spherical; however, the particles obtained using the present invention appear more discrete and are an order of magnitude smaller than particles in FIGS. 9a and b. As with the results obtained in the previous example, particle diameter is again narrowly distributed around 1 $\mu$m. Thus, the present invention produces smaller particles than the conventional process with less agglomeration, a property that is desirable, especially in the pharmaceutical industry.

Example 3

Recrystallization of Ibuprofen from a DMSO Solution Using the Present Invention in which Compressed $CO_2$ Was Used as Energizing Gas and as Antisolvent FIGS. 11a and b show a pair of SEM micrographs of Ibuprofen particles recrystallized from a 30 mg/ml DMSO solution under the same operating conditions as in Example 2, section 2.2. Once again, particles appear to be discrete, particle sizes are small and, except for a fraction of micron-sized particles, most particles are smaller and in the range of 0.6 $\mu$m or less.

Example 4

Recrystallization of Camptothecin from a DMSO Solution Using the Present Invention is which Compressed $CO_2$ Was used as Energizing Gas and as Antisolvent Camptothecin, as supplied by the vendor, appears as amorphous particles with diameters ranging from 1–10 $\mu$m. FIG. 12 is an SEM micrograph of camptothecin particles recrystallized from a 5 mg/ml DMSO solution under the same operating conditions as in Example 2, section 2.2 (i.e., P=1,500 psig, 35° C. with a $CO_2$ back pressure of roughly 100 psig). Particles are nearly spherical and discrete. Although relatively large in size (5–20 $\mu$m), these particles appear to be porous. The relatively high surface area of these particles should increase their dissolution rate and bioavailability.

Figure 7B:
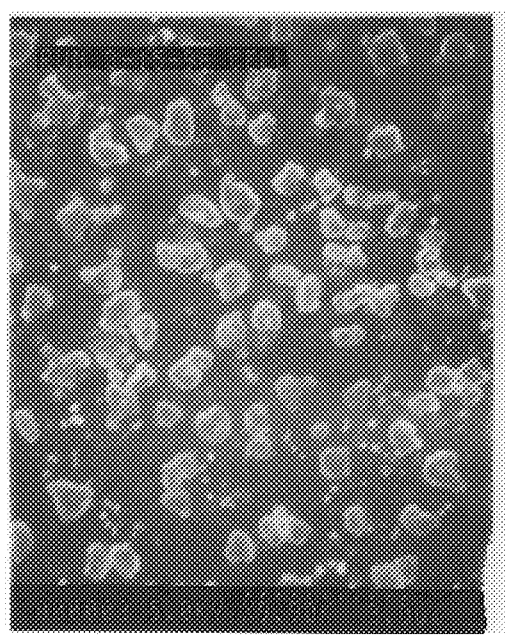
Figure 13B:
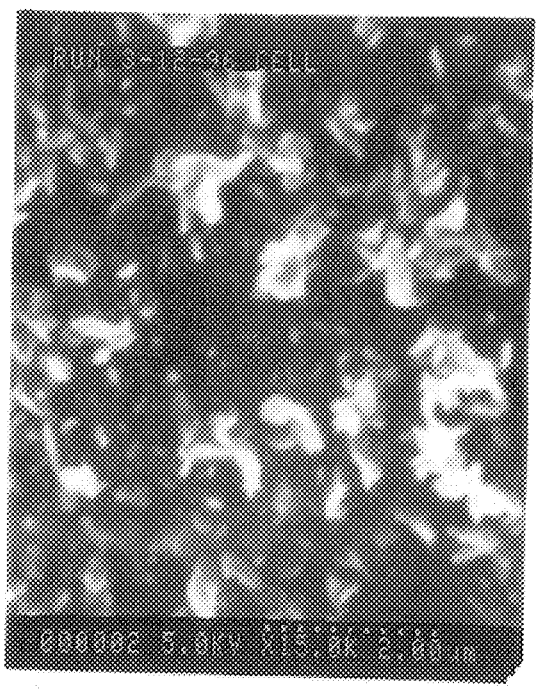

FIGS. 3a and b show a pair of SEM micrographs of camptothecin particles recrystallized from a 5 mg/ml DMSO solution under the same operating conditions as in Example 1, FIGS. 7 and 8 (i.e., P=1,250 psig, T=35° C., with a $CO_2$ back pressure of 600 psig). Because of the higher expansion and velocities of the compressed gas (from 1,850 psig to 1,250 psig compared to 1,600 psig to 1,500 psig in the previous experiment), smaller particles are formed. As seen in FIG. 13b, particles are non-agglomerated with the average diameter in the range of 0.5 $\mu$m. Here again, as in Example 1 where favorable operating conditions were used, nanoparticles were produced.

ALTERNATIVE EMBODIMENTS

Note that in an alternative process, the chamber contains liquid $CO_2$ or other liquid antisolvent as opposed to supercritical $CO_2$ or another antisolvent in its supercritical form. In this case, the volume above the liquid phase (i.e., the vapor phase) contains mostly the light gas or the antisolvent which powers the nozzle of the present invention, and recrystallization takes place in either the liquid phase (when a light gas is used to power the spray nozzle) or in both phases (when an antisolvent is used to power the spray nozzle). In the case where the antisolvent itself is used to power the nozzle, operating conditions are such that the energizing gas at its near-critical or supercritical state will nearly attain the conditions in the recrystallization chamber upon expansion through the nozzle. This alternative process is attractive for applications where containment of the recrystallized particles in the crystallization chamber is difficult because of entrainment in the supercritical phase. The lower buoyancy of liquids compared to supercritical fluids can minimize losses of small micro-sized or nano-sized particles.

OTHER APPLICATIONS FOR THE INVENTIVE METHOD AND APPARATUS DISCLOSED HEREIN

This invention finds application in areas where reduction in particle size to below 1 $\mu$m is desired for the purpose of increasing the surface area, the rate of dissolution, reactivity, or bioavailability.

The disclosed invention also finds application in areas where recrystallization of microparticles or nanoparticles from organic solutions is desirable. These applications can find use in the production of foods, electronic equipment, explosives, pharmaceutical products or intermediates (micronization, nanonization, coating, microencapsulation, lyophilization, and co-precipitation), catalysts (micronization and nanonization to increase the surface area of active sites or support), explosives (improved reactivity), coating (finer coatings), polymers (micronization and nanonization), pesticides (micronication, nanonization, and microencapsulation), and other chemicals (micronization, nanonization, and microencapsulation).

Antisolvents useful in the application of this invention include, but are not limited to, $CO_2$, propane, butane, isobutane, $CHF_3$, $SF_6$, and $N_2O$. Organic solvents may be either of the class of aromatic hydrocarbons, alcohols, esters, ethers, ketones, amines, or nitrated or chlorinated hydrocarbons. Preferred solvents include acetone, ethanol, methanol, dichloromethane, ethyl acetate and DMSO.

CONCLUSION

The method and apparatus of the present invention overcome the disadvantages associated with conventional GAS processes in several ways. The high-velocity wave-front and/or turbulence established at the exit of the nozzle by the energizing gas breaks up the solution exiting the nozzle into a fine spray of droplets. The mass transfer rate between the spray droplets and the surrounding antisolvent phases is essentially proportional to the surface area of the spray droplets, and the antisolvent and solute concentration gradients. Use of the nozzle of the present invention provides a means for enhancing mass transfer rates through an increase in both the surface area of the spray and the interphase concentration gradients.

One effect of the creation of the small size droplets is to increase the specific surface area of the droplets, that in turn increases the rate of mass transfer. Also, in contrast to the electrically energized nozzle which produces a relatively low velocity spray, the compressed energizing gas passes the atomized droplets as it enters the supercritical antisolvent at high velocity and thereby creates a turbulence which prevents a build-up of depleted solvent in the proximity of the atomized spray. An increase in the concentration gradients between the droplet phase and the antisolvent phase provides an increased driving force for interphase mass transfer.

Other advantages of the compressed gas-powered nozzle of the present invention over other nozzles in their use for recrystallization of solutes from organic solutions or suspensions are:

1. The relatively large size of the line through which the solution flows through the nozzle compared to either capillary or micro-orifice nozzles allows for higher solution throughput and reduces the probability of nozzle plugging.
2. The same fluid can be used for both energizing the spray nozzle as well as an anti-solvent.
3. The high velocity of the energizing gas stream imparts a high velocity to the spray droplets, and therefore reduces the tendency for droplet coalescence which can lead to the formation of larger particles.
4. The high velocity of the gas or supercritical fluid energizing stream provides a buffer zone at the tip of the nozzle that is either a gas or a low-density supercritical fluid. If the gas has little or no antisolvent power, the buffer zone at the tip of the nozzle serves to delay recrystallization until after secondary atomization of the spray has been achieved. This case is most attractive when using highly viscous or concentrated (nearly saturated or supersaturated) solutions.

If the energizing gas is itself a supercritical fluid antisolvent, the buffer zone is a highly turbulent zone of nearly pure antisolvent, thereby maximizing mass transfer rates between the droplets and the antisolvent while minimizing the droplet coalescence rate. This case is most attractive when recrystallizing drugs or polymers from solutions with low solute concentrations. Use of a compressed gas with intermediate antisolvent power (i.e. a mixture of light gas and antisolvent) provides a means for controlling interphase mass transfer rates, and therefore means for controlling particle size.

The teachings of all references cited herein and those cited in the Provisional Application Ser. No. 60/012,593 (identified above), and all references cited therein, are incorporated herein by reference.

The theories expressed above are offered for the purpose of assisting with the understanding of the invention. It is to be understood, however, that the scope of the invention as disclosed and claimed herein is not limited by or restricted to such theories which are subject to change.

We claim:

1. In a process for the production of particles, said process comprising the step of spraying a solution including at least one solvent and at least one solute through a nozzle into an antisolvent, the improvement comprising the steps of:

generating atomized droplets of said solution; and contacting said droplets with said antisolvent to produce particles having an average diameter of 0.6 μm or less.

2. In a process for the production of particles, said process comprising the step of spraying a solution including at least one solvent and at least one solute through a nozzle into an antisolvent, the improvement comprising:

combining said solution with a compressed fluid to produce a mixture;

passing said solution through a nozzle to produce atomized droplets of the mixture; and contacting said droplets with said antisolvent to produce said particles.

3. In a process for the production of particles, said process comprising the step of spraying a solution including at least one solvent and at least one solute through a nozzle into an antisolvent, the improvement comprising:

combining said solution with a compressed fluid to produce a mixture;

passing said mixture through a nozzle to establish at the nozzle exit a wave-front, said wave-front producing atomized droplets; and contacting said droplets with said antisolvent to produce said particles.

4. A method for producing particles, said method comprising the steps of:

providing a solution including at least one solvent and at least one solute;

providing an antisolvent;

providing a compressed fluid;

providing a nozzle for atomizing said solution, said nozzle having:

a first inlet for receiving said solution, a second inlet for receiving said compressed fluid, an exit; and means configured to receive and combine said solution and said compressed fluid from said first and second inlets, respectively;

introducing said solution and said compressed fluid into said nozzle first and second inlets, respectively, to produce a mixture;

passing said mixture out of said nozzle exit to produce atomized droplets;

contacting said droplets with said compressed fluid outside said nozzle exit to cause depletion of said solvent from said droplets; and contacting said droplets with said antisolvent to cause further depletion of said solvent from said droplets to produce said particles.

5. The method of claim 4, said step of contacting said droplets with said antisolvent effected by contacting said droplets with a flowing stream of said antisolvent.

6. The method of claim 4, a wave-front being produced by said mixture when said mixture passes out of said nozzle exit.

7. The method of claim 6, said wave-front being produced by said mixture when said mixture passes out of said nozzle exit at a near-sonic, sonic, or ultrasonic velocity.

8. The method of claim 6, said wave-front having a frequency greater than 15 kHz.

9. The method of claim 4, said atomized droplets produced in said passing step having an average diameter of 0.1–10 μm.

10. The method of claim 4, said nozzle including a convergent-divergent channel extending between said nozzle inlets and exit, and configured to produce said wave-front.

11. The method of claim 4, said antisolvent being selected from the group consisting of a near-critical fluid and a supercritical fluid.

12. The method of claim 11, said supercritical fluid being selected from the group consisting of carbon dioxide, propane, butane, isobutane, nitrous oxide, sulfur hexafluoride, and trifluoromethane.

13. The method of claim 11, said near-critical fluid being selected from the group consisting of carbon dioxide, propane, butane, isobutane, sulfur hexafluoride, and triflуromethane.

14. The method of claim 4, said antisolvent including a surfactant.

15. The method of claim 4, said compressed fluid being selected from the group consisting of air, oxygen, nitrogen, helium, carbon dioxide, propane, butane, isobutane, trifluromethane, nitrous oxide, sulfur hexafluoride, and combinations thereof.

16. The method of claim 4, said compressed fluid being a light gas selected from the group consisting of air, oxygen, nitrogen, helium, or combinations thereof, said compressed fluid being used to energize said nozzle, and being used to produce a buffer zone between said atomized droplets and said antisolvent, the rate of said depletion occurring in said buffer zone being less than the rate of said depletion occurring in said antisolvent.

17. The method of claim 4, said compressed fluid being a mixture of a light gas and an antisolvent.

18. The method of claim 4, said compressed fluid being an antisolvent.

19. The method of claim 4, said particles having an average diameter of 10 $\mu$m or less.

20. The method of claim 4, said particles having an average diameter of 0.6 $\mu$m or less.

21. The method of claim 4, said solute being a pharmaceutical drug.

22. The method of claim 21, said pharmaceutical drug being selected from the group consisting of Cyclosporin A, hydrocortisone, ibuprofen, poly-lactide glycolide copolymers, hyaluronic acid derivatives, and camptothecin.

* * * * *